(12) United States Patent
Dellea et al.

(10) Patent No.: US 9,652,865 B2
(45) Date of Patent: May 16, 2017

(54) OPTICAL METHOD FOR CHARACTERIZING A DIFFRACTIVE SURFACE AND APPARATUS FOR IMPLEMENTING SUCH A METHOD

(71) Applicant: COMMISSARIAT A L'ENERGIE ATOMIQUE ET AUX ENERGIES ALTERNATIVES, Paris (FR)

(72) Inventors: Olivier Dellea, La Talaudiere (FR); Simon-Frédéric Desage, Saint-Chamond (FR); Pascal Fugier, Bernin (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 37 days.

(21) Appl. No.: 14/782,478

(22) PCT Filed: Mar. 26, 2014

(86) PCT No.: PCT/IB2014/060164
§ 371 (c)(1),
(2) Date: Oct. 5, 2015

(87) PCT Pub. No.: WO2014/162241
PCT Pub. Date: Oct. 9, 2014

(65) Prior Publication Data
US 2016/0063733 A1     Mar. 3, 2016

(30) Foreign Application Priority Data

Apr. 5, 2013  (FR) ...................... 13 53075

(51) Int. Cl.
*G06K 9/00*  (2006.01)
*G06T 7/40*  (2017.01)
(Continued)

(52) U.S. Cl.
CPC .......... *G06T 7/40* (2013.01); *G01N 21/4788* (2013.01); *G06T 7/0004* (2013.01);
(Continued)

(58) Field of Classification Search
None
See application file for complete search history.

(56) References Cited

U.S. PATENT DOCUMENTS 5,576,543 A     11/1996  Dingley
7,463,369 B2 *  12/2008  Wack .................... G01B 11/24
                                                        356/364

(Continued)

FOREIGN PATENT DOCUMENTS

FR     3 002 800 A1    9/2014
JP     2004 286483 A   10/2004
WO     WO 2012/113745 A1  8/2012

OTHER PUBLICATIONS

International Search Report and Written Opinion for corresponding International Patent Application No. PCT/IB2014/060164 dated May 26, 2014.

*Primary Examiner* — Weiwen Yang
(74) *Attorney, Agent, or Firm* — Alston & Bird LLP

(57) ABSTRACT

An optical method for characterizing a diffractive surface having a crystal grain structure, including the steps of: a) successively illuminating said surface with a plurality of light beams (Fi) having propagation directions inclined by a same angle Θ; relative to the normal to the surface and of which the projections on the surface form azimuth angle φi that are different relative to a reference direction; b) acquiring an image of the surface corresponding to each of the light beams; and c) digitally processing images to obtain at least one item of information on at least one property of the surface chosen from: the grain structure, texture and level of (Continued)

ordering thereof. An optical head (TO) and apparatus for implementing such a method.

13 Claims, 7 Drawing Sheets

(51) Int. Cl.
    *G01N 21/47*     (2006.01)
    *G06T 7/00*     (2017.01)
    *G02B 1/00*     (2006.01)
    *G02B 5/18*     (2006.01)

(52) U.S. Cl.
    CPC .... *G06T 7/0085* (2013.01); *G01N 2021/4711* (2013.01); *G01N 2021/4735* (2013.01); *G02B 1/005* (2013.01); *G02B 5/1847* (2013.01); *G02B 2207/101* (2013.01); *G06T 2207/10028* (2013.01); *G06T 2207/10056* (2013.01); *G06T 2207/20136* (2013.01); *G06T 2207/30108* (2013.01)

(56) References Cited

U.S. PATENT DOCUMENTS

| | | | |
|---|---|---|---|
| 2005/0053974 A1* | 3/2005 | Lakowicz | G01N 21/4788 435/6.12 |
| 2006/0186362 A1* | 8/2006 | Bills | G01N 21/21 250/559.46 |
| 2009/0290156 A1* | 11/2009 | Popescu | G01N 15/1434 356/338 |

\* cited by examiner

OPTICAL METHOD FOR CHARACTERIZING A DIFFRACTIVE SURFACE AND APPARATUS FOR IMPLEMENTING SUCH A METHOD

FIELD

The invention relates to an optical method for characterizing a diffracting surface having a grain structure, and to an apparatus for implementing this method and to an optical head of said apparatus. The invention in particular applies to the characterization and monitoring of the manufacture of assemblies of particles of nanoscale or micron-size dimensions on a substrate.

BACKGROUND

The order of compact assemblies of colloidal particles is important in a wide variety of applications: photonic crystals, SERS (surface-enhanced Raman scattering) sensors, biological sensors, etc.

At the present time, the order of diffracting structures, such as compact assemblies of colloidal particles, may be measured only using optical-type microscopy techniques or using a scanning electron microscope. These techniques are not suitable for the characterization of structures occupying large areas (several centimeters square or more).

SUMMARY

The Applicant has developed a process allowing compact films of micron-size or nanoscale particles to be transferred to flexible or rigid substrates. Such a process is described in document WO2012113745 and illustrated by FIG. 1, in which may be seen:
- a system SD allowing particles NP dispersed in a liquid in order to form a suspension SC to be dispensed;
- a liquid conveyor CL, formed by a flow of a "carrier" liquid, which may be different from that in which the particles NP are dispersed, for transporting and arranging the particles in order to form a compact film FP. This liquid conveyor flows over an inclined plane then through a horizontal zone called the transfer zone ZT; and
- a flexible substrate SF made to move by a conveyor to which the compact film of particles must be transferred. The link between the carrier liquid and the substrate is ensured by a capillary bridge PC.

The process therefore consists in dispensing the particles onto the surface of the carrier liquid. The carrier liquid transports the particles as far as the transfer zone. The particles accumulate in the transfer zone, then also in the lower portion of the inclined plane. The particles present on the inclined plane then exert a pressure that helps order the particles present in the transfer zone. A variant of the process allows a rigid substrate to be used.

FIG. 2 shows a micrograph of a film of silica microspheres (diameter: 1.1 µm) deposited on a silicon substrate. It may be seen that the particles organize into a compact hexagonal configuration in which each particle is surrounded by 6 neighbors the centers of which form a hexagon.

In practice, the films of particles produced are made up of "grains" that comprise particles forming a regular lattice of hexagonal unit cells the orientation of which in the plane is specific. The grains differ from one another in the orientation of the elementary unit cell of their lattice. The size of the grains may vary from a few $\mu m^2$ (microns square) to as much as 1 $cm^2$ (centimeter square) or more; it depends on the size dispersion of the particles and on the parameters of the process (surface pressure, draw rate, activation of the particles, etc.). FIG. 3 shows two grains, G1 and G2, separated by a boundary F. It will furthermore be noted that the grains do not necessarily have a perfectly periodic structure, but are characterized by a variable degree of order, which may be expressed by a number comprised between 0 (completely irregular amorphous arrangement) and 1 (perfectly periodic or "crystalline" arrangement).

When the constituent particles of such a film have suitable dimensions (in the case of spherical particles of silica on a liquid conveyor formed by water, a diameter comprised between about 500 nm and 2.5 µm), it is possible to observe light diffraction effects. The grain structure of the film then results in iridescence forming a random pattern.

The invention aims to provide a method allowing a compact film of micron-sized or nanoscale particles—or more generally a diffracting surface—to be characterized by validation of its structure (related to the shape of the grains), its texture (related to the orientation of the elementary unit cell of each grain) and/or its degree of order. The degree of order is defined as the ratio of the area of regions having a desired orientation to the total observed area. A method according to the present invention is an alternative to that described in French patent application 13/51870 filed on the 1st Mar. 2013.

According to the invention, such an aim is achieved by a method for characterizing a diffracting surface having a "crystal" grain structure, comprising steps consisting in:

a) illuminating in succession said surface with N>1 light beams having propagation directions inclined at the same angle $\theta_i$ to the normal to the surface and the projections of which onto the surface make different azimuthal angles $\phi_i^j$ to a reference direction;

b) acquiring an image of said surface in correspondence with each of said light beams in a given acquisition direction; and c) digitally processing said images to obtain at least one piece of information on at least one property of said surface, chosen from: its grain structure, its texture and its degree of order;

characterized in that said step c comprises determining, for each point of said surface corresponding to a pixel of said images, an average azimuthal angle of a range of azimuthal angles $\phi_i^j$ for which said point appears bright when it is observed in said acquisition direction.

According to various embodiments of this method:
  Said step c) may comprise, for each point of said surface corresponding to a pixel of said images, substeps consisting in:
  c1) constructing a binary vector containing N elements each associated with one of said light beams, each element of this vector being representative of the light intensity of said pixel when the surface is illuminated by the corresponding light beam, the element taking a first binary value if said intensity is lower than a threshold and a second binary value if it is higher than said threshold; and
  c2) determining said average azimuthal angle from said vector.
  Said substep c2) may comprise identifying, in said vector, a block of contiguous elements having said second binary value and determining a central element of said block, said average azimuthal angle being that of the light beam associated with said central element.

Each of said grains may have a two-dimensional periodicity with hexagonal symmetry and in which said azimuthal angles $\phi_i^j$ are given by: $\phi_i^j=\phi_0+j\cdot(60°/N)$, where the index j ranges from 1 to N and $\phi_0$ is a constant.

The number N of light rays used may be higher than or equal to 3, and preferably higher than or equal to 6.

In said step b), said images may be acquired in an observation direction normal to the surface to be characterized.

Said step c) may also comprise automatically detecting those regions of said diffracting surface which are formed by points characterized by the same said average azimuthal angle, said regions being identified with crystal grains.

Said step c) may also comprise automatically detecting outlines of said regions of said diffracting surface, said outlines being identified with grain boundaries.

Said step c) may also comprise calculating a degree of order of said diffracting surface, said degree of order being defined as the difference between the proportion of points of said surface corresponding to pixels of said images identified as belonging to crystal grains, and the proportion of points of said surface corresponding to pixels of said images identified as belonging to grain boundaries.

Said surface to be characterized may be formed by an assembly of particles of nanoscale or micron-size dimensions on a substrate.

Said surface to be characterized may especially be formed by an assembly of particles of nanoscale or micron-size dimensions on a substrate.

Another subject of the invention is the application of such a method to the monitoring of a process for manufacturing an assembly of particles of nanoscale or micron-size dimensions. The method according to the invention may be used to characterize the assembly deposited on a substrate, resulting from the manufacturing process, or indeed to carry out inline monitoring of said manufacturing process, by characterizing the assembly in a piece of equipment of the type in FIG. 1 before its deposition.

Yet another subject of the invention is an apparatus for implementing such a method, comprising:

an optical head suitable for generating a plurality of light beams having propagation directions inclined at the same angle $\theta_i$ to the normal to a diffracting surface to be characterized, and the projections of which onto the surface make different azimuthal angles $\phi_i^j$ to a reference direction;

a camera, having an optical axis coincident with said axis of symmetry, arranged to acquire an image of said surface in correspondence with each of said light beams; and a means for digitally processing the images acquired by said camera in order to obtain at least one piece of information on at least one property of said surface, chosen from: its grain structure, its texture and its degree of order; said digitally processing means being configured or programmed to determine, for each point of said surface corresponding to a pixel of said images, an average azimuthal angle of a range of azimuthal angles $\phi_i^j$ for which said point appears bright when it is observed in said acquisition direction.

The digitally processing means may especially be an opportunely programmed conventional computer, an electronic board for digitally processing images or even a dedicated digital circuit. dr

BRIEF DESCRIPTION OF THE DRAWINGS

Other features, details and advantages of the invention will become apparent on reading the description given with reference to the appended drawings, in which.

DETAILED DESCRIPTION

Figure 1:
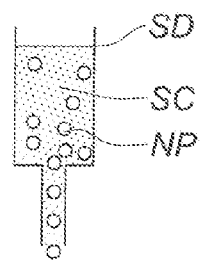
FIG. 1 shows a method for transferring of compact films of micron-size or nanoscale particles to be transferred to a flexible or rigid substrate.
Figure 1:
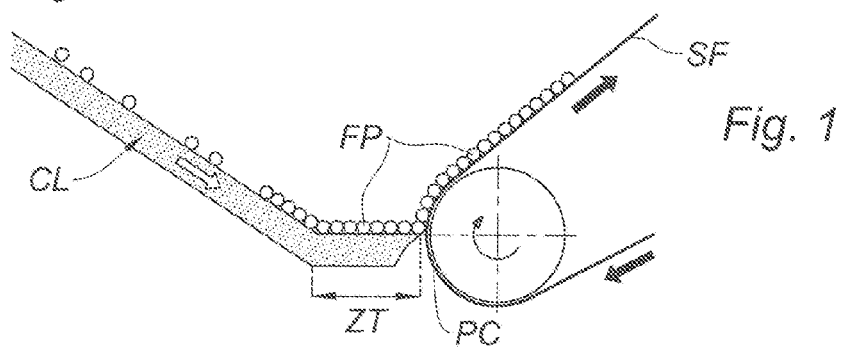
Figure 2:
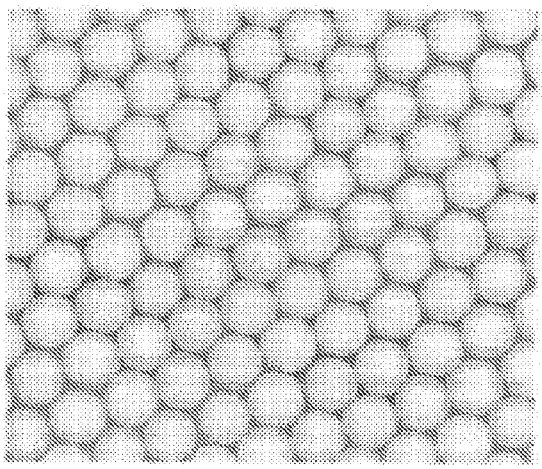
FIG. 2 shows a micrograph of a film of silica microspheres deposited on a silicon substrate.
Figure 3:
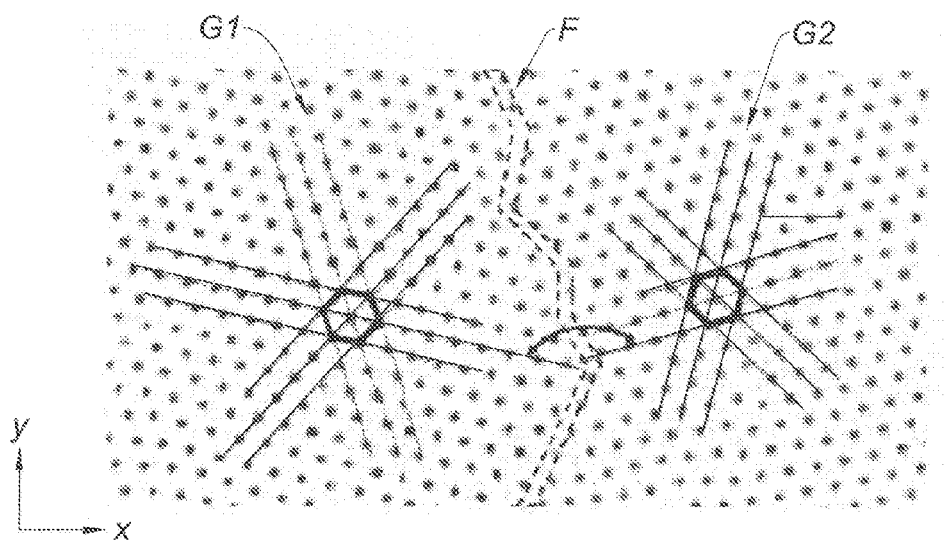
FIG. 3 shows two grains separated by a boundary.
Figure 4A:
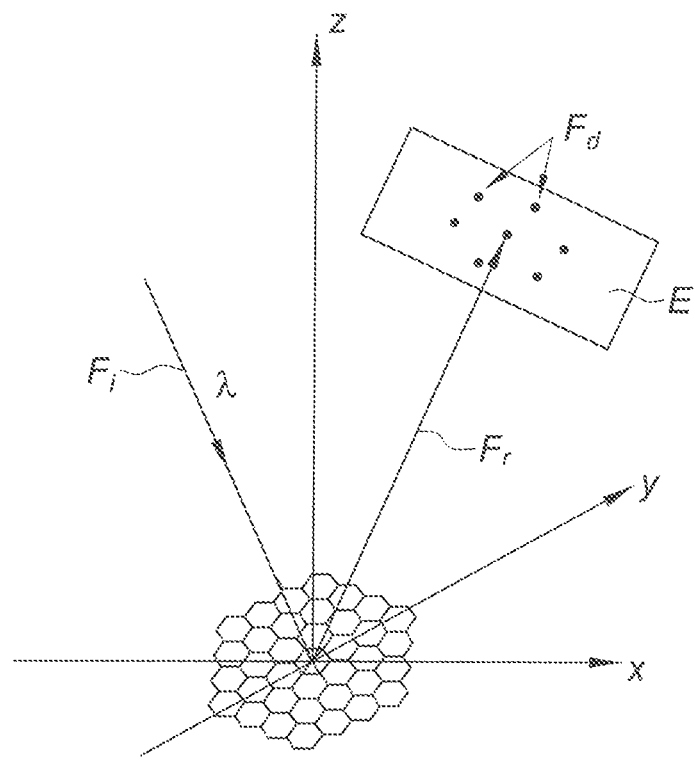
FIGS. 4A-4C illustrate the effect of diffraction by a structure able to be characterized according to the invention.

When an incident light beam $F_i$ of wavelength $\lambda$ illuminates a periodic structure such as a film of particles, the light beam is diffracted into a plurality of orders (diffracted beams $F_d$) the number of which depends on the number of periods that the structure comprises. In the case of a structure having hexagonal symmetry (case of a film of particles arranged to form compact hexagonal assemblies), for example, diffraction of the first order occurs in 6 spatial directions, forming a hexagonal pattern on a screen E placed normal to the reflected beam (see FIG. 4A). This pattern corresponds to the Fourier transform of the image of the periodic structure.

Figure 4B:
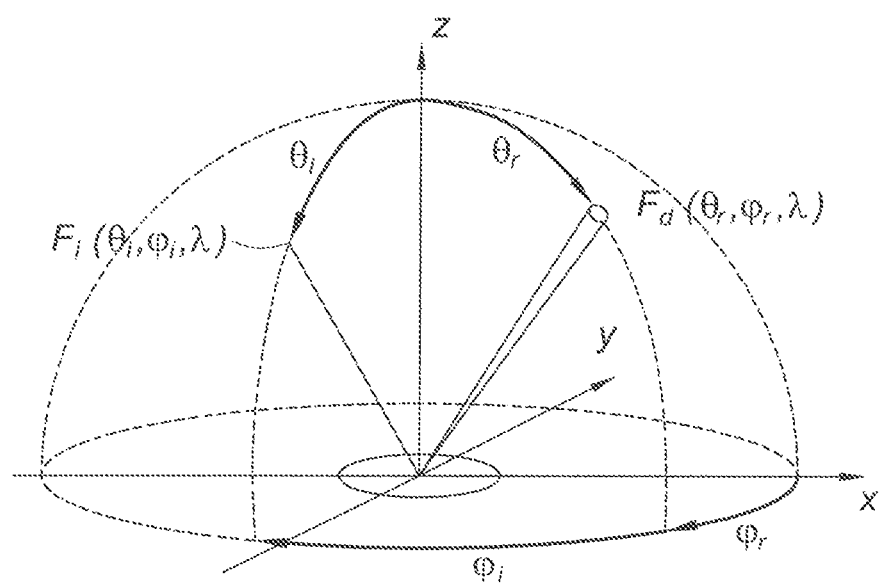

When a periodic structure of this type is illuminated with a polychromatic incident beam (comprising a plurality of wavelengths), each wavelength is diffracted in a spatial direction that is specific thereto. The following formulae give the orientation of the diffracted beams $F_d$ relative to the incident beam $F_i$:

$$\theta_r = \arcsin\left[\frac{\sqrt{(m\lambda - d\sin\theta_i\cos\varphi_i)^2 + (n\lambda - d\sin\theta_i\sin\varphi_i)^2}}{d}\right]$$

$$\varphi_r = \arctan\left[\frac{-d\sin\theta_i\sin\varphi_i + \lambda n}{-d\sin\theta_i\cos\varphi_i + \lambda m}\right]$$

where $\lambda$ is the wavelength in question (nm);

d the lattice parameter, i.e. the distance between the centers of two particles of the film (nm);

$(\theta_i, \phi_i)$ the inclination of the incident beam to the normal to the diffracting film and its azimuthal angle, respectively (see FIG. 4B);

$(\theta_r, \phi_r)$ the angles defining the direction of the diffracted beam (see FIG. 4B); and (n,m) integers defining the diffraction spots, order and position. The diffraction spots are defined for the 1st order by (n,m)=(1,1), (−1,−1), (0,1), (0,−1), (1,0), (−1, 0); for the 2nd order (n,m)=(2,2) . . . (and so on, just like for the spots of the first order but replacing the "1's" with "2's").

Figure 4C:
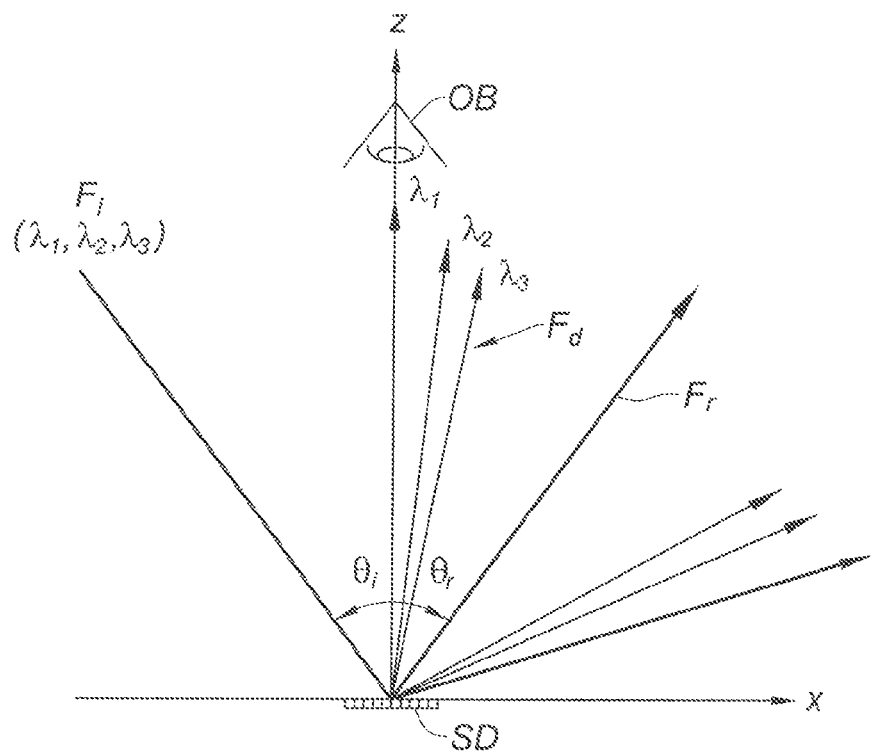

When a diffracting surface SD is illuminated with a polychromatic beam (wavelengths $\lambda_1$, $\lambda_2$, $\lambda_3$, etc.) at an angle of incidence $\theta_i$, an observer OB located normal to the structure sees the wavelength at which the above equations give $\theta_r=0$; if none of the illuminating wavelengths meets this condition, the structure appears black to the observer. This is illustrated in FIG. 4C.

For a given lattice parameter "d", the angle $\theta_i$ determines the wavelength (the color) of the radiation detected by the observer OB, whereas $\phi_i$—azimuthal angle of the incident beam relative to the spatial orientation of the elementary crystal unit cell of the diffracting structure—determines the intensity of said detected radiation. Thus, the brightness of each grain of the diffracting structure will depend on its orientation. Thus, acquiring a plurality of images corresponding to different azimuthal angles q allows the diffracting surface to be characterized by identifying grains (structural information), their orientation (textural information) and their degree of order. This is one principle behind the present invention.

Figure 5:
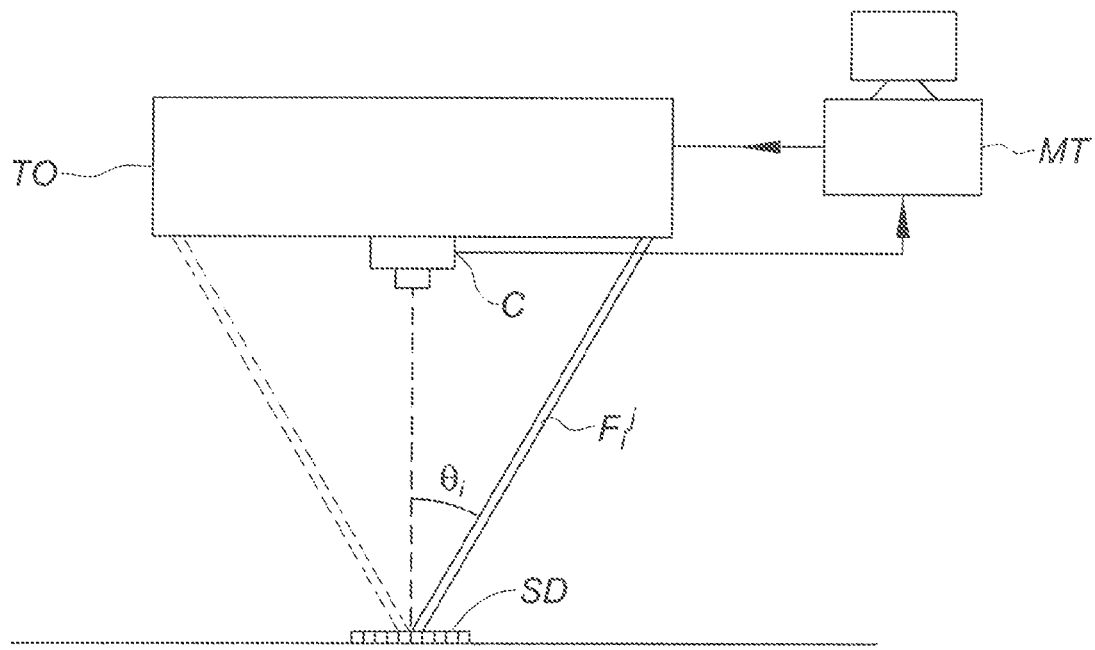
FIG. 5 illustrates, generally, an apparatus for characterizing a diffracting structure according to one embodiment of the invention.

FIG. 5 schematically shows an apparatus for implementing a characterizing method according to the invention. This apparatus essentially comprises three elements:
  an optical head TO capable of generating a plurality of light beams $F_i^j$ having the same inclination $\theta_i$ to the normal to the diffracting surface SD to be characterized, but different azimuthal angles $\phi_i^j$;
  a camera C observing the surface SD (or more precisely its portion illuminated by the light beams generated by the optical head) in an observation direction perpendicular to said surface; and
  a data-processing means MT processing the images acquired by the camera C in order to obtain the required structural, textural and order information, and if need be for controlling the optical head TO. It may especially be a question of an opportunely programmed conventional computer, or indeed of a dedicated electronic board.

Figure 6A:
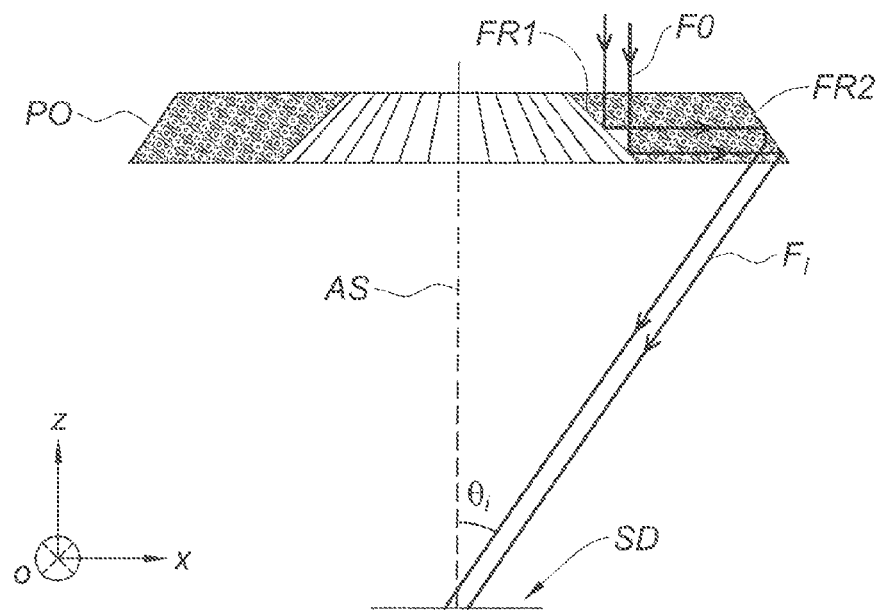
FIGS. 6A-6D show a first embodiment of an optical head of such an apparatus.
Figure 6B:
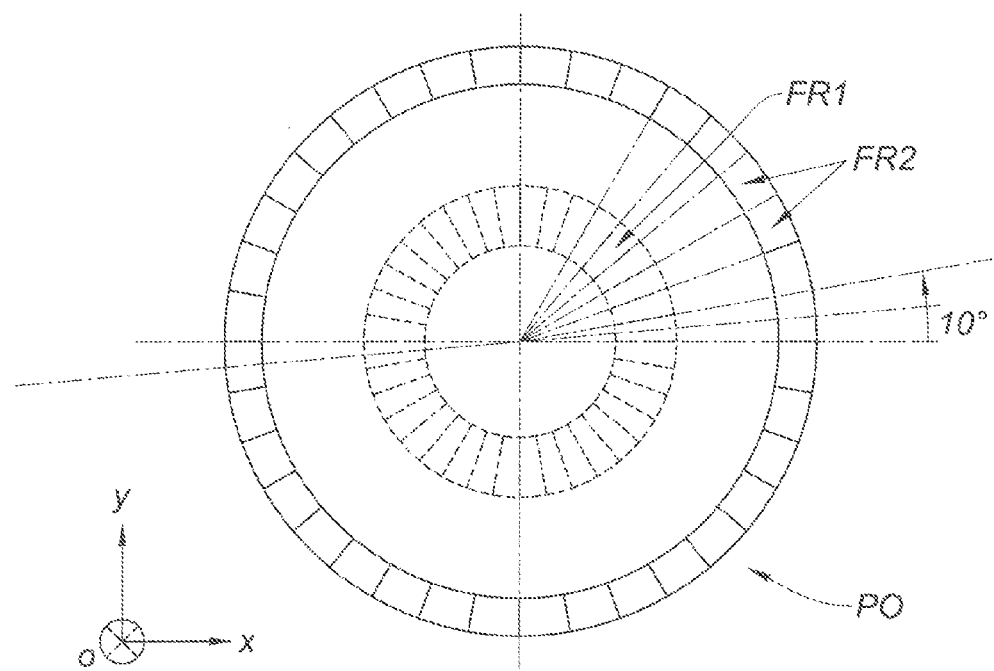
Figure 6C:
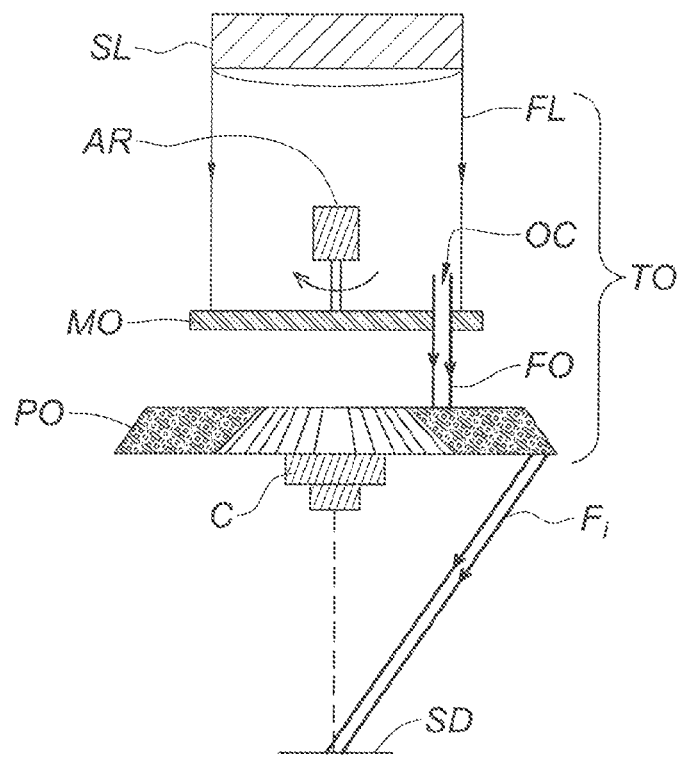

FIGS. 6A-6C illustrate the structure and operation of an optical head TO, already described in the aforementioned French patent application 13/51870, able to be used to implement the method of the invention.

The essential element of this optical head is a transparent part PO (FIG. 6A: cross-sectional view; FIG. 6B: top view) having an axis of symmetry AS intended to coincide with the optical axis of the camera C, and therefore to be perpendicular to the diffracting surface SD. This part, which is for example made of glass or Plexiglas or polycarbonate or polymethyl methacrylate (PMMA), comprises a first array of M reflective facets FR1 arranged about the axis AS and inclined such that their normals make an angle of about 45° to the latter, so as to form a truncated pyramid. The part also has a second array of M reflective facets FR2, arranged around said axis AS and said first array; the second array of facets may form the lateral surface of the part. The facets FR2 are inclined such that their normals make an angle of about 45° to the axis of symmetry AS, so as to form another truncated pyramid. Furthermore, each facet FR2 is placed facing a respective facet FR1. Considering a light beam F0 that propagates parallel to the axis AS, but that is shifted laterally relative to said axis, and that penetrates into the part PO via its top side, it is reflected by a facet FR1 and propagates in a radial direction relative to the axis AS until reaching a facet FR2 that reflects it downward. The beam—indicated below by $F_i$—then exits from the bottom side of the part (while being deviated by refraction), and propagates, at an angle $\theta_i$ to the axis AS, in the direction of the diffracting surface SD to be characterized, which is located under the part PO.

The inclination of the facets FR2 is chosen such that the angle $\theta_i$ has the desired value, which is generally comprised between 10° and 80°, preferably between 25° and 50°, and which may especially be 34°. It must not be forgotten to take into account the refraction of the beam when it exits the part P0.

Assuming now that the beam F0 is moved such that its point of entry into the part PO traces a circle centered on the axis AS, each time the illuminated facet FR1 changes, the azimuthal angle of the beam $F_i$ in turn changes. Considering for example the case where each array of the part comprises M=36 facets, such that the angle made by two consecutive facets is 10°, under these conditions 36 beams $F_i$ having azimuthal angles spaced by steps of 10° will possibly be obtained.

Figure 6D:
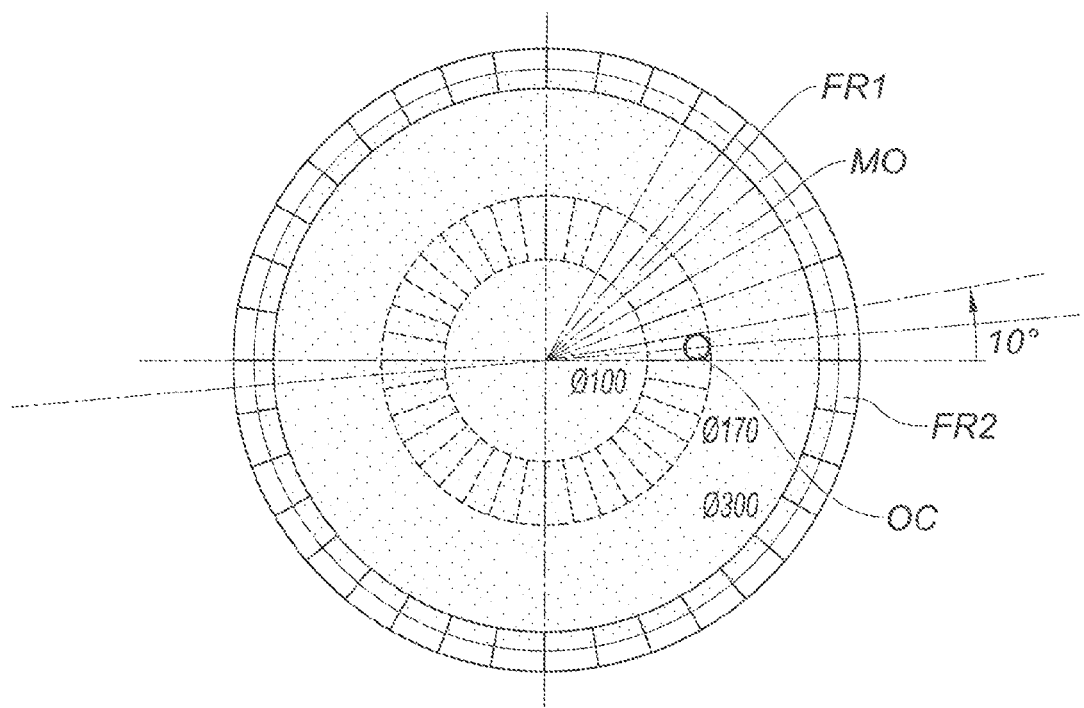

The selective illumination of the facets of the optical part may be obtained in a plurality of different ways. One particularly simple solution, illustrated in FIGS. 6C and 6D, consists in placing above the optical part PO a disk-shaped optical mask MP containing a, for example circular, aperture OC located at a distance from the axis AS tailored so that it lies plumb with a facet FR1. A motor AR makes the disk rotate about the axis AS, and a light source SL illuminates it with a collimated light beam FL of sufficiently large cross section, propagating parallel to said axis. FIG. 6C shows a side view of the optical head allowing the operation thereof to be understood, whereas FIG. 6D is a top view of the optical part PO and the mask MO.

The light beam FL may be polychromatic and spatially incoherent and for example be a beam of incoherent white light. In this case, the source SL may especially be a light-emitting diode. The use of a monochromatic source such as a laser may lead to a better analysis performance, but experiments have shown that white light leads to satisfactory results while allowing simpler and less expensive equipment to be used.

The camera C that acquires the images may be fastened to the center of the bottom surface of the part PO. It is important for the images to be acquired when a single facet FR1 and a single facet FR2 are illuminated, and not during the transitions.

A diffracting surface of hexagonal structure must, in order to be able to be satisfactorily characterized, be illuminated at a plurality of angles of incidence over a period of 60°. It has been verified that it is enough to acquire 6 images with six light beams having azimuthal angles $\phi_i^j = j \cdot 10° = 10°$, 20°, 30°, 40°, 50°, 60°; more generally, N beams with $\phi_i^j = \phi_0 + j \cdot (60°/N)$, $\phi_0$ being a constant, will possibly be used. N must in general be higher than or equal to 3, and preferably higher than or equal to 6. As a general rule, the higher the value of N the more precise the characterization of the surface but the longer the processing and acquisition time. Generally, it therefore does not seem to be advantageous to make N higher than 12 or even 24.

Figure 7:
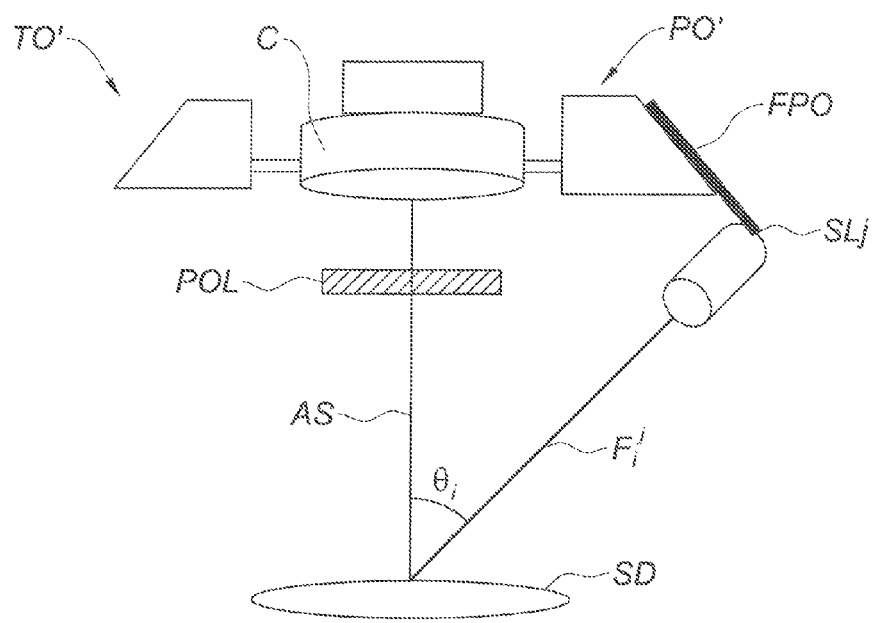
FIG. 7 shows a second embodiment of an optical head of such an apparatus.

FIG. 7 shows a cross-sectional view of an optical head TO' having an alternative structure. This optical head TO' comprises an optionally transparent part PO', which is for example made of aluminum, having a shape that is generated by revolution (for example a ring shape) and faceted on its periphery and the facets FPO of which bear N light sources $SL_j$—for example light-emitting diodes and especially white light-emitting diodes—arranged regularly about the axis of revolution and oriented obliquely toward said axis of revolution. The light sources $SL_j$ (j=1−N) generate directly the N (typically N=6) incident light beams $F_i^j$ having azimuthal angles $\phi_i^j$, as in the case of the optical head TO described above. The acquiring camera C is arranged as in the case of said optical head TO.

The optical head in FIG. 7 may also be used to implement the method described in the aforementioned French patent application 13/51870.

Whatever the embodiment of the optical head, and whatever the characterizing method in question, it is advantageous to place a linear polarizer POL in front of the camera C in order to filter parasitic light and prevent saturation of the sensor of said camera. Specifically, diffracted light is partially polarized, whereas scattered light is not; a linear polarizer therefore makes it possible to improve the ratio (intensity of diffracted light)/(intensity of scattered light).

In operation, i.e. when the illumination is turning around the zone of the surface in question, the processing means is continuously processing at least 6 images taken consecutively and stored in a FIFO (First In, First Out) stack. In other words, once a block of 6 images has been analyzed, image No 1 is erased, the numbers of the remaining images are decremented by 1 and a new image having the number 6 in the image file is considered. The analysis is carried out each time the stack is updated.

Figures 8A, 8B:
FIGS. 8A-8D illustrate an image-processing algorithm allowing a diffracting structure to be characterized according to one embodiment of the invention.

FIG. 8A shows the six images stored in the stack, corresponding to azimuthal angles of illumination $\phi_i^j=j\cdot10°=10°$, 20°, 30°, 40°, 50°, 60°. The images shown here are grayscale images, but they may also be color images and show an iridescence effect.

The first step of the processing consists in thresholding the images in the stack in order to obtain a black-and-white image, the white pixels corresponding to points of the surface that appear bright ("high" diffracted light intensity, i.e. higher than a threshold) and the black pixels corresponding to points that appear dark ("low" light intensity, i.e. lower than said threshold): see FIG. 8B.

The second step of the processing consists in constructing, for each pixel of said images (or, more exactly, for each point of the surface corresponding to a pixel of said images), a binary vector of size N. The jth element of this vector is equal to "1" if the pixel is white when the surface is illuminated at the azimuthal angle $\phi_i^j$ and "0" in the contrary case. For example, if the vector associated with a pixel of coordinates $(x_0, y_0)$ is: [0 1 1 1 0 0], this means that this pixel is white for an illumination of azimuthal angle equal to 20°, 30° and 40° and black in the other cases.

The third step consists in determining the central or average illumination direction of the range of directions for which the pixel is white. This is done by considering the associated vector to have a circular structure (the first element is considered to follow on immediately from the latter), by identifying a block of successive elements having the value 1 (second, third and fourth elements in the case of the vector [0 1 1 1 0 0]) and by determining a "central" element of said block (the third element corresponding to an azimuthal direction of 30° in the considered example). If the block of "ones" contains an even number of elements, there are two elements that could be considered as "central"; then one of the two will be arbitrarily but consistently chosen.

The following is an algorithm for automatically determining the central or average illumination direction in which the pixel is white:

The vector is duplicated: thus from the vector [0 1 1 1 0 0] containing N=6 elements a vector [0 1 1 1 0 0 0 1 1 1 0 0] containing 2N=12 components is obtained;

Each element of the duplicated vector is multiplied by an integer indicative of its position (equivalently, the duplicated vector is multiplied element by element by the vector [1 2 3 . . . 12]; thus the vector of integers [0 2 3 4 0 0 0 8 9 10 0 0] is obtained;

Next, the N=6 successions of N=6 elements contained in the vector thus obtained are considered: [0 2 3 4 0 0]; [2 3 4 0 0 0]; [3 4 0 0 0 8]; [4 0 0 0 8 9]; [0 0 0 8 9 10]; [0 0 8 9 10 0] and [0 8 9 10 0 0];

The sum of these elements divided by the number of nonzero elements modulo N is associated with each of said successions: [0 2 3 4 0 0]→ (2+3+4)/3 mod 6=3; [2 3 4 0 0 0]→(2+3+4)/3 mod 6=3; [3 4 0 0 0 8]→(3+4+8)/3 mod 6=5; [4 0 0 0 8 9]→(4+8+9)/3 mod 6=7 mod 6=1; [0 0 0 8 9 10]→(8+9+10)/3 mod 6=9 mod 6=3; [0 0 8 9 10 0]→(8+9+10)/3 mod 6=3 and [0 8 9 10 0 0]→(8+9+10)/3 mod 6=3; this therefore yields one times the value 1, four times the value 3 and one times the value 5;

The value that has the highest frequency (here the value 3) is retained, this value indicating the desired central or average illumination direction—here $\phi_i^j|_{j=3}=30°$. If two values have the same frequency the highest or lowest is chosen arbitrarily (but consistently from one pixel to another). For example, in the case of a vector [0 1 1 1 1 0] the central or average illumination direction may be considered to be equal to 30°, 40° or even 35°.

Thus, with each pixel of the image is associated a numerical value V comprised between 1 and 7 (more generally between 1 and N+1); for V comprised between 1 and 6, this value corresponds to the index "j" of the central or average illumination direction: $\phi_i^j|_{j=V}$; the case V=7 identifies the case where the pixel is entirely black or entirely white. The latter case may correspond to three distinct situations: either this pixel of the camera is defective; or the pixel appears entirely black because it corresponds to an "empty" region that does not reflect light; or the pixel appears entirely white because it corresponds to an amorphous region that scatters light instead of diffracting it. Generally, a "defective pixel" is spoken of.

Figure 8C:
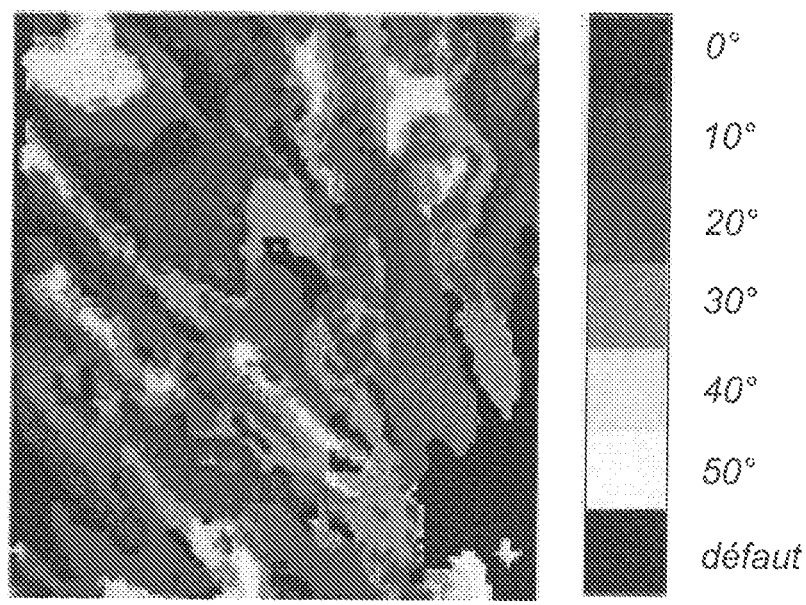
Figure 8D:
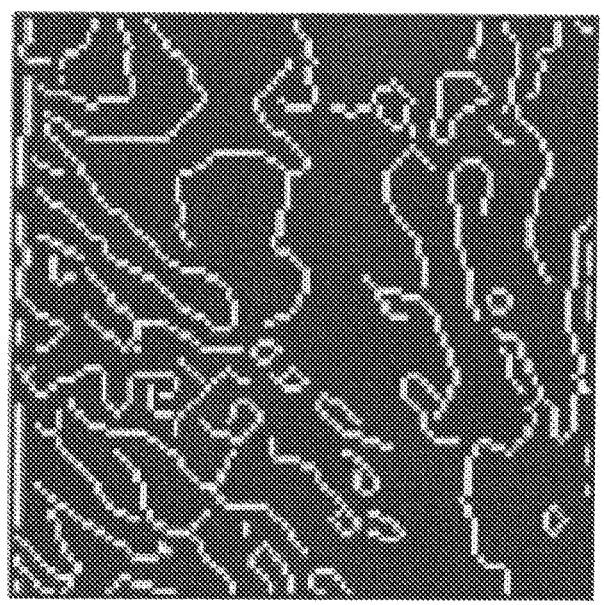

FIG. 8C is a "false-color" image of the surface, in which each gray level corresponds to a different value of the parameter V. This image contains all the information on the texture of the surface. It is possible to apply thereto an outline-detecting algorithm, known per se, in order to determine the structure of the surface. This is illustrated in FIG. 8D, in which the black zones correspond to crystal grains (whatever their orientation) or to "defective" (amorphous or empty) regions, and the white lines to grain boundaries.

The following procedure is used to determine the degree of order:

T1, defined as the ratio of the number of pixels corresponding to a defined crystal orientation (black pixels in FIG. 8D, excluding "defective" pixels, i.e. pixels that are black in FIG. 8C) to the total number of pixels of the image, is calculated;

T2, defined as the one's complement of the ratio of the number of pixels corresponding to a grain boundary (white pixels in FIG. 8D, excluding "defective" pixels) to the number of pixels corresponding to a defined crystal orientation (black pixels in FIG. 8D, again excluding "defective" pixels), is calculated;

The degree of order is given by the product of T1 and T2: ORD=T1×T2=(number of pixels belonging to one orientation− number of pixels corresponding to a grain boundary)/total number of pixels.

In a conventional way, image-processing steps aiming to improve or optimize the quality of the images will possibly be associated with the protocol described above. These steps will for example aim to decrease illumination drift in order to increase the reliability of the analysis.

A plurality of variants of the protocol may be envisioned. These variants may relate to the illumination conditions of the surface (use of mono- or polychromatic or spatially coherent or incoherent radiation etc.) and/or the processing of the acquired data (for example, algorithms other than the one described above may be used to determine the "central" illumination direction).

The method of the invention is particularly suitable for monitoring in real time a process for manufacturing regular assemblies of nano- and micro-particles such as the process described in document WO2012113745. Specifically, the optical head may be easily integrated into an apparatus for implementing such a process; furthermore, sufficiently large areas of diffracting surface (of 1 cm$^2$ or more) may be characterized. However, this is not a limitation, and the invention may be suitable for many other applications.

The invention claimed is:

1. A method for characterizing a diffracting surface having a grain structure, comprising the steps:
   a) illuminating in succession said surface with N>1 light beams ($F_i^j$) having propagation directions inclined at the same angle $\theta_i$ to the normal to the surface and the projections of which onto the surface make different azimuthal angles $\phi_i^j$ to a reference direction;
   b) acquiring an image of said surface in correspondence with each of said light beams in a given acquisition direction; and
   c) digitally processing said images to obtain at least one piece of information on at least one property of said surface, chosen from: its grain structure, its texture and its degree of order;
   wherein said step c) comprises determining, for each point of said surface corresponding to a pixel of said images, an average azimuthal angle of a range of azimuthal angles $\phi_i^j$ for which said point appears bright when it is observed in said acquisition direction.

2. The method as claimed in claim 1, in which said step c) comprises, for each point of said surface corresponding to a pixel of said images, substeps comprising:
   c1) constructing a binary vector containing N elements each associated with one of said light beams, each element of this vector being representative of the light intensity of said pixel when the surface is illuminated by the corresponding light beam, the element taking a first binary value if said intensity is lower than a threshold and a second binary value if it is higher than said threshold; and
   c2) determining said average azimuthal angle from said vector.

3. The method as claimed in claim 2, in which said substep c2) comprises identifying, in said vector, a block of contiguous elements having said second binary value and determining a central element of said block, said average azimuthal angle being that of the light beam associated with said central element.

4. The method as claimed in claim 1, in which each of said grains has a two-dimensional periodicity with hexagonal symmetry and in which said azimuthal angles $\phi_i^j$ are given by: $\phi_i^j = \phi_0 + j \cdot (60°/N)$, where the index j ranges from 1 to N and $\phi_0$ is a constant.

5. The method as claimed in claim 1, in which the number N of light rays used is higher than or equal to 3.

6. The method as claimed in claim 1, in which, in said step b), said images are acquired in an observation direction normal to the surface to be characterized.

7. The method as claimed in claim 1, in which said step c) also comprises automatically detecting those regions of said diffracting surface which are formed by points characterized by the same said average azimuthal angle, said regions being identified with crystal grains.

8. The method as claimed in claim 7, in which said step c) also comprises automatically detecting outlines of said regions of said diffracting surface, said outlines being identified with grain boundaries.

9. The method as claimed in claim 6, in which said step c) also comprises calculating a degree of order of said diffracting surface, said degree of order being defined as the difference between the proportion of points of said surface corresponding to pixels of said images identified as belonging to crystal grains, and the proportion of points of said surface corresponding to pixels of said images identified as belonging to grain boundaries.

10. The method as claimed in claim 1, in which said surface to be characterized is formed by an assembly of particles of nanoscale or micron-size dimensions on a substrate.

11. The application of a method as claimed in claim 10 to the monitoring of a process for manufacturing an assembly of particles of nanoscale or micron-size dimensions on a substrate.

12. An apparatus for implementing a method as claimed in claim 1, comprising:
    an optical head configured for generating a plurality of light beams ($F_i^j$) having propagation directions inclined at the same angle $\theta_i$; to the normal to a diffracting surface to be characterized, and the projections of which onto the surface make different azimuthal angles $\phi_i^j$ to a reference direction;
    a camera, having an optical axis coincident with said axis of symmetry, arranged to acquire an image of said surface in correspondence with each of said light beams; and
    a means for digitally processing the images acquired by said camera in order to obtain at least one piece of information on at least one property of said surface, chosen from: its grain structure, its texture and its degree of order; said digitally processing means being configured or programmed to determine, for each point of said surface corresponding to a pixel of said images, an average azimuthal angle of a range of azimuthal angles $\phi_i^j$ for which said point appears bright when it is observed in said acquisition direction.

13. The method as claimed in claim 1, in which the number N of light rays used is higher than or equal to 6.

* * * * *